(12) United States Patent
Stack et al.

(10) Patent No.: US 11,135,421 B2
(45) Date of Patent: Oct. 5, 2021

(54) CONDUIT FOR TRANSSEPTAL PASSAGE OF DEVICES TO THE AORTA

(71) Applicant: Synecor LLC, Chapel Hill, NC (US)

(72) Inventors: Richard S Stack, Chapel Hill, NC (US); William L Athas, Chapel Hill, NC (US); Kevin Johnson, Durham, NC (US); Emer M Feerick, Galway (IE); Matthew Moran, Galway (IE); Richard Phelan, Kilkenny (IE)

(73) Assignee: Synecor LLC, Durham, NC (US)

( * ) Notice: Subject to any disclaimer, the term of this patent is extended or adjusted under 35 U.S.C. 154(b) by 0 days.

(21) Appl. No.: 16/578,374

(22) Filed: Sep. 22, 2019

(65) Prior Publication Data
US 2020/0254160 A1 Aug. 13, 2020

Related U.S. Application Data

(60) Provisional application No. 62/802,212, filed on Feb. 7, 2019.

(51) Int. Cl.
*A61M 1/10* (2006.01)
*A61M 1/12* (2006.01)
(Continued)

(52) U.S. Cl.
CPC ....... *A61M 60/857* (2021.01); *A61B 17/3468* (2013.01); *A61F 2/2427* (2013.01); *A61M 25/09* (2013.01); *A61M 60/135* (2021.01); *A61M 60/148* (2021.01); *A61B 2017/00243* (2013.01); *A61B 2017/00327* (2013.01); *A61M 25/10* (2013.01); *A61M 2210/125* (2013.01)

(58) Field of Classification Search
CPC .... A61M 1/1008; A61M 1/122; A61M 1/125; A61M 2210/125; A61M 2210/127; A61M 25/09; A61B 17/3468; A61B 2017/00243; A61B 2017/00327; A61F 2/2427
See application file for complete search history.

(56) References Cited

U.S. PATENT DOCUMENTS

| 4,117,836 | A | * | 10/1978 | Erikson | A61B 6/504 600/435 |
| 4,568,338 | A | * | 2/1986 | Todd | A61M 25/04 604/530 |

(Continued)

*Primary Examiner* — Quynh-Nhu H. Vu

(57) ABSTRACT

A conduit for creating a passage from a right atrium to a left atrium, through a mitral valve into the left ventricle, and to provide a passage from the left ventricle into the aortic valve. The conduit includes an elongate tubular member having a shaft with a proximal section and a distal loop section at a distal end of the proximal section. The distal loop section includes a proximal curve, a distal curve, a generally straight segment extending between the curves, and a distal tip. The shaft in the distal loop section curves back on itself so that proximal curve is formed by a part of the shaft that is closer along the length of the shaft to the distal tip. The shapes of the proximal and distal curves are selected to direct the distal tip into the mitral valve after it has crossed the inter-atrial septum from the right atrium to the left atrium of the heart, and to orient the distal opening of the distal tip towards the aortic valve when the proximal curve is in the mitral valve and the distal tip is in the left ventricle.

18 Claims, 8 Drawing Sheets

(51) Int. Cl.
*A61M 60/857* (2021.01)
*A61B 17/34* (2006.01)
*A61F 2/24* (2006.01)
*A61M 25/09* (2006.01)
*A61M 60/135* (2021.01)
*A61M 60/148* (2021.01)
*A61M 25/10* (2013.01)
*A61B 17/00* (2006.01)

(56) References Cited

U.S. PATENT DOCUMENTS

| | | | | |
|---|---|---|---|---|
| 4,694,838 A * | 9/1987 | Wijayarthna | A61M 5/007 | 600/435 |
| 4,738,667 A * | 4/1988 | Galloway | A61M 25/04 | 604/530 |
| 4,898,591 A * | 2/1990 | Jang | A61L 29/049 | 604/264 |
| 5,052,998 A * | 10/1991 | Zimmon | A61M 25/04 | 604/8 |
| 5,163,431 A * | 11/1992 | Griep | A61M 25/0041 | 600/435 |
| 5,171,232 A * | 12/1992 | Castillo | A61M 25/0054 | 378/162 |
| 5,215,530 A * | 6/1993 | Hogan | A61M 25/02 | 604/174 |
| 5,401,258 A * | 3/1995 | Voda | A61M 25/0041 | 604/523 |
| 5,480,392 A * | 1/1996 | Mous | A61M 25/0041 | 600/435 |
| 5,658,263 A * | 8/1997 | Dang | A61M 25/0041 | 604/264 |
| 5,868,700 A * | 2/1999 | Voda | A61M 25/0041 | 604/510 |
| 5,876,385 A * | 3/1999 | Ikari | A61M 25/0041 | 604/523 |
| 6,004,280 A * | 12/1999 | Buck | A61M 25/0041 | 600/434 |
| 6,036,682 A * | 3/2000 | Lange | A61M 25/0108 | 604/264 |
| 6,106,510 A * | 8/2000 | Lunn | A61M 25/0012 | 600/433 |
| 6,475,195 B1 * | 11/2002 | Voda | A61M 25/0041 | 604/264 |
| 7,729,782 B2 * | 6/2010 | Williams | A61M 25/0041 | 607/122 |
| 8,948,848 B2 * | 2/2015 | Merhi | A61F 2/013 | 600/435 |
| 2003/0199849 A1 * | 10/2003 | Hackett | A61M 25/0069 | 604/523 |
| 2004/0044350 A1 * | 3/2004 | Martin | A61B 1/0057 | 606/139 |
| 2008/0208166 A1 * | 8/2008 | Goode | A61M 25/0662 | 604/510 |
| 2010/0268017 A1 * | 10/2010 | Siess | A61M 60/205 | 600/16 |
| 2012/0016342 A1 * | 1/2012 | Brecker | A61M 25/09025 | 604/528 |
| 2014/0088566 A1 * | 3/2014 | Dangoisse | A61M 25/0041 | 604/532 |
| 2016/0022961 A1 * | 1/2016 | Rosenman | A61M 25/0141 | 604/95.04 |
| 2016/0135865 A1 * | 5/2016 | Jannicke | A61B 18/1492 | 606/21 |
| 2017/0087334 A1 * | 3/2017 | Tegg | A61B 5/6852 | |
| 2017/0112461 A1 * | 4/2017 | McDonald | A61B 6/481 | |

\* cited by examiner

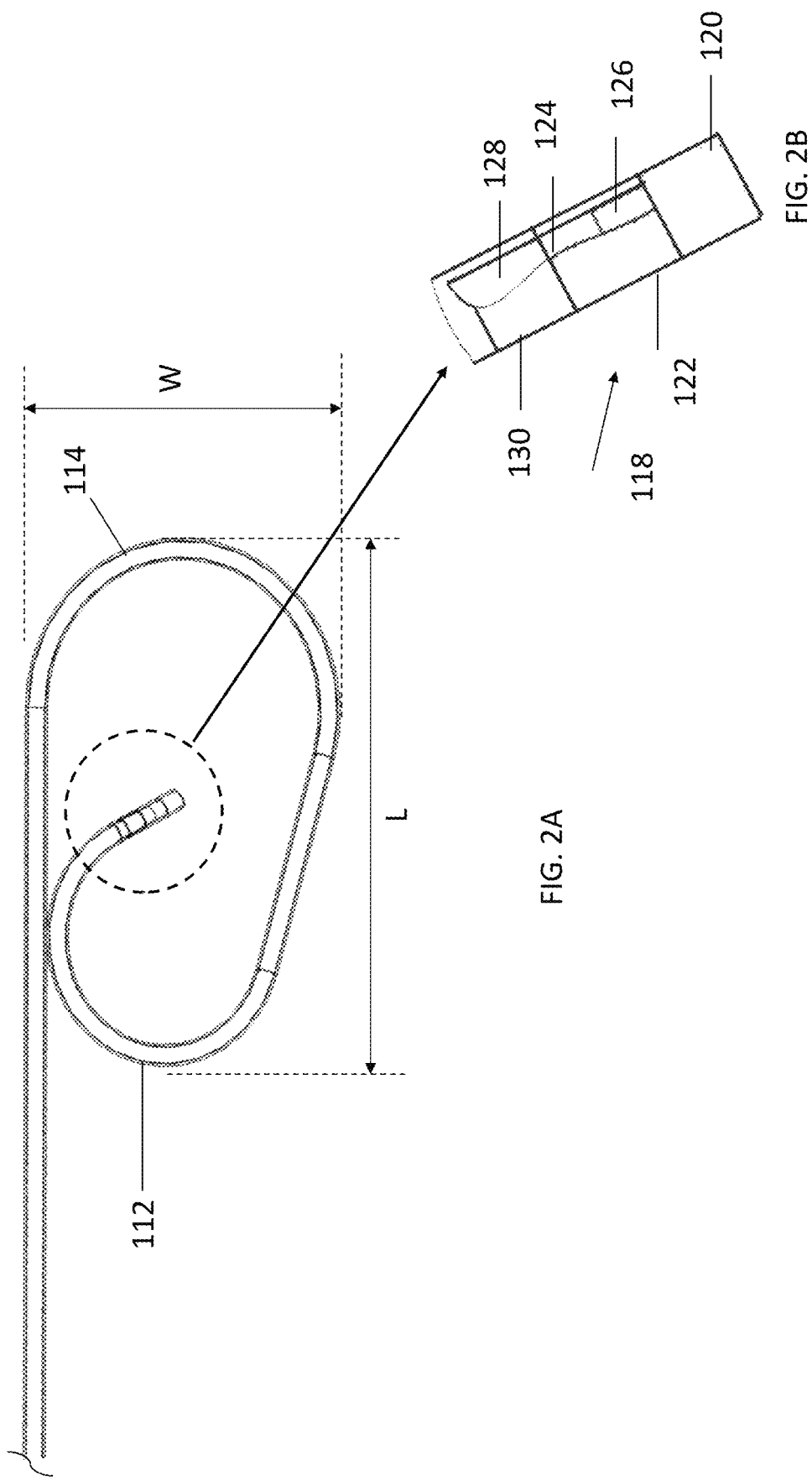

CONDUIT FOR TRANSSEPTAL PASSAGE OF DEVICES TO THE AORTA

This application claims the benefit of U.S. Provisional Application No. 62/802,212, filed Feb. 7, 2019, which is incorporated hereby reference.

BACKGROUND

Various medical procedures in use today involve passage of devices from the right side of the heart to the left side across the inter-atrial septum in a well-established technique known as transseptal catheterization.

Commonly owned application Ser. No. 16/578,375, Systems and Methods for Transseptal Delivery of Percutaneous Ventricular Assist Devices and Other Non-Guidewire Based Transvascular Therapeutic Devices, filed Sep. 22, 2019, which is incorporated herein by reference, discloses a system and method for delivering therapeutic devices positionable at the aortic valve, and gives as a primary example its use to deliver pVADs. In that application, transseptal catheterization is used to deliver a long flexible cable such that it extends from the venous vasculature through the heart to the arterial vasculature. Once positioned the cable has one end extending from the right subclavian vein and an opposite end extending from the right or left femoral artery. Once positioned in this way, a grasper is attached to the cable at the femoral artery, and the cable is withdrawn from the right subclavian vein to position the grasper along the route previously occupied by the cable. The grasper is then attached at the right subclavian vein to a pVAD and pulled from the femoral artery while the pVAD is simultaneously pushed at the right subclavian vein. This combination of pulling and pushing force moves the pVAD into the heart, across the septum and the mitral valves, and into its final position at the aortic valve.

Commonly owned co-pending application PCT/US2017/62913, filed Nov. 22, 2017, published as WO/2018/098210 (incorporated herein by reference) discloses a system and method for delivering mitral valve therapeutic devices to the heart (such as devices for positioning a replacement mitral valve or devices for treating a native mitral valve) using a transseptal approach. In that application, transseptal catheterization is used to position a cable that is used to deliver a therapeutic device to the mitral valve site. Once the cable is positioned it has one end extending from the right femoral vein and an opposite end extending from the left or right femoral artery. The mitral valve therapeutic device is attached to the cable at the right femoral vein. The cable is then pulled at the femoral artery while the mitral valve therapeutic device is simultaneously pushed at the right femoral vein. This combination of pulling and pushing force moves the mitral valve therapeutic device into the heart, across the septum and to its final position at the mitral valve.

In each of the above procedures, the step of pulling the cable and the grasper are carried out with those devices extending through a protective device (referred to in those applications as a left ventricle redirector "LVR")) having the features described in those applications. This avoids disruption of the valve structures when tension is applied to the grasper or cable.

In each of the above procedures, a Brockenbrough type of transseptal catheterization is initially performed using access from the right femoral vein, and then other devices make use of the transseptal access created to aid in positioning of the wire or cable that is to ultimately reach the aorta and femoral artery. A common challenge of these procedures is the need to provide safe passage for such devices downwardly within the left atrium from the transseptal puncture site towards the mitral valve, and then through the mitral valve and upwardly within the left ventricle to the aortic valve, without engaging the delicate chordae tendineae of the mitral valve, and then into the aorta beyond the level of the coronary sinuses to the aortic arch and descending aorta. This application describes a right to left conduit (RLC) configured to navigate this passage, while possessing material properties that resist kinking and transmit the torque needed to achieve delivery with minimal impact to the chordae or endocardial tissue.

BRIEF DESCRIPTION OF THE DRAWINGS

FIG. 2A is a side elevation view of the distal part of the RLC.

FIG. 2B is a partially cut-away view of the region of the RLC encircled in FIG. 2A.

FIGS. 3A through 6 are a series of figures schematically illustrating steps in which the RLC is used to help deliver a cable device that is to be passed through the heart between the venous and arterial vasculature, in which:

FIG. 3A illustrates transseptal advancement of a wire through a Brockenbrough transseptal catheter and into the left atrium.

FIG. 4 illustrates the position of the RLC in the left ventricle oriented towards the aortic valve. The arrows in FIG. 4 represent the "windshield wiper" motion of the distal tip of the RLC after it passes through the mitral valve but before the wire is advanced through it into the aortic valve.

FIG. 5 illustrates the steps of using a balloon catheter for an atrial septostomy and then to confirm that the path traversed by the wire is free from chordae entrapment.

FIG. 6 illustrates the step of advancing a snare over the RLC in preparation for use of the snare to capture and retrieve the end of a cable advanced through the RLC.

DETAILED DESCRIPTION

Figure 1:
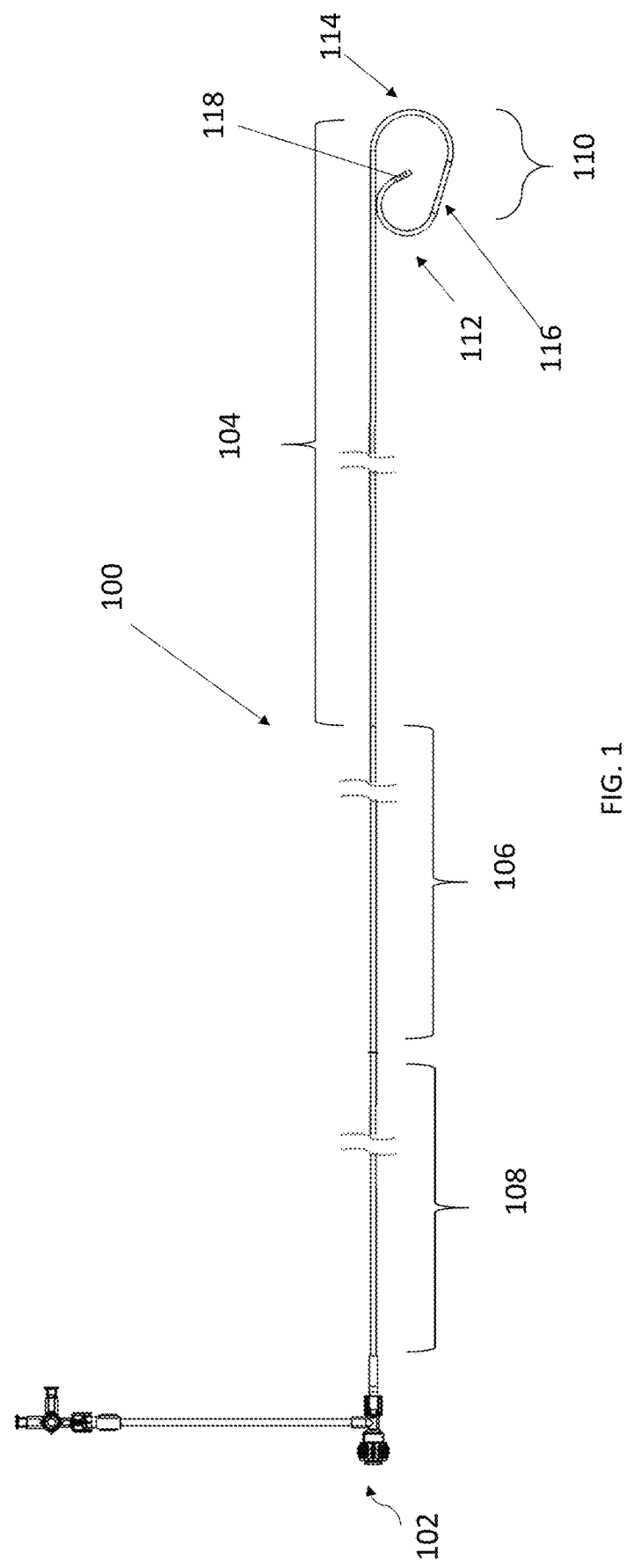
FIG. 1 is a side elevation view of a Right-to-Left conduit ("RLC").

Referring to FIG. 1 the Right-to-Left conduit 100 ("RLC") is an elongate tubular catheter having a length sufficient to permit it to extend from the RFV of a human adult to the right atrium, across the interatrial septum (via a trans-septal puncture) to the left atrium, through the mitral valve, left ventricle, aortic valve to the aortic arch, and then to the descending aorta. In a preferred embodiment, this length exceeds 150 cm, and it may be 160 cm or longer. A lumen extends through the RLC 100 from a proximal port 102 to an opening at the distal end. A flush port is also fluidly connected with the lumen of the RLC as shown.

The RLC has a distal portion 104, an intermediate portion 106, and a proximal portion 108. The proximal and intermediate portions, 108, 106 and much of the distal portion 104, are of generally straight tubular construction. These parts of the shaft may be collectively referred to as the main body of the shaft. The distal portion 104 includes a distal loop 110 that has been shape set. The shape of the loop helps the distal end of the RCL pass into the mitral valve after it has crossed the inter-atrial septum from the right to the left side of the heart, further aids in orienting the distal opening of the RLC towards the aortic valve (as will be discussed in connection with FIG. 4) when the distal part of the RLC is in the left ventricle.

More particularly, the distal loop 110 includes a distal (where for the purposes of this description of the curves of the RLC the term "distal" and "proximal" are used in regard to the entire length of the catheter) curve in regard to the entire length of the catheter 112, a more proximal curve 114, a generally straight segment 116 extending between the curves, and a distal tip 118. The RLC is shape set with the longitudinal axes of the distal and proximal curves in a common plane as shown in FIG. 2D, although in alternative embodiments such as the embodiment shown in FIG. 2E they might lie in different planes. In other embodiments, one or both of the curves might be formed with a shape where the longitudinal axis forms a three-dimensional shape and thus does not lie within a single plane. The generally straight segment 116 may be straight or it may be curved with a very large radius of curvature to produce a significantly more gradual curve than the proximal and distal curves.

The curves 112, 114 are arranged to cause the distal loop 110 to curve back on itself, so that the distal curve 112 is formed by a part of the RLC shaft that is closer along the length of the shaft to the distal tip 118 than is the proximal curve 114. The radius of the distal curve is smaller than that of the proximal curve, so that the lateral width (perpendicular to the longitudinal axis of the straight section of the shaft) of the loop 110 tapers inwardly from a proximal to distal direction. The distal tip is preferably enclosed within the loop, bounded by distal and proximal curves, segment 116, and the main body of the shaft. It is also, preferably, oriented with its distal opening facing away from the main body of the shaft.

Referring to FIG. 2A, the radii of the distal and proximal curves, the length of the generally straight segment 116 along its longitudinal axis, the widest lateral dimension W of the distal loop (measured in a direction perpendicular to the longitudinal axis of the straight part of the RLC), and the longitudinal length L of the distal loop (in a direction parallel to the longitudinal axis of the straight part of the RLC) are proportioned so that when the proximal curve 114 is within mitral valve, the distal curve 112 is positioned in the left ventricular outflow tract (as shown in 3B) and the tip 118 is oriented towards, and in close proximity to, the aortic valve. In one embodiment, length L may be in the range of 65-95 mm, with a preferred range of approximately 70-90 mm, or more preferably approximately 75-85 mm. Width W may be in the range of 35-65 mm, with a preferred range of approximately 40-60 mm, or more preferably approximately 45-55 mm. The radius of the distal curve 112 may be in the range of 5-35, with a preferred range of 10-30 mm, and a most preferred range of 15-25 mm. The radius of the proximal curve 114 may be in the range of 10-40 mm, with a preferred range of 15-35 mm, and a most preferred range of 20-30 mm.

Figure 2C:
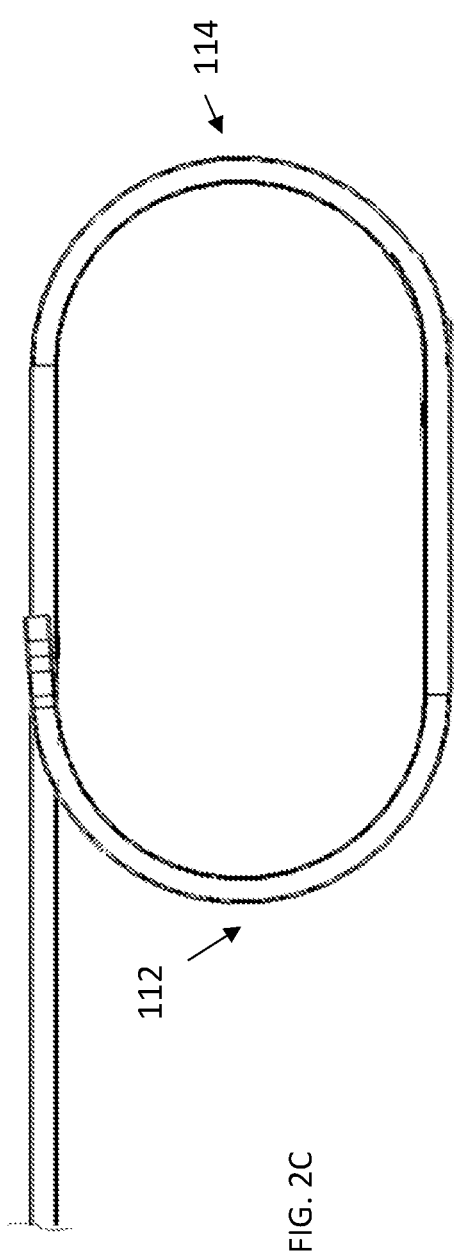
FIG. 2C is a side elevation view similar to FIG. 2A, but showing an alternative configuration in which the widest lateral dimension of the distal curve is approximately equal to the widest lateral dimension of the proximal curve
Figure 2D:
FIG. 2D is a side elevation view taken ninety degrees from the view of FIG. 2A.
Figure 2E:
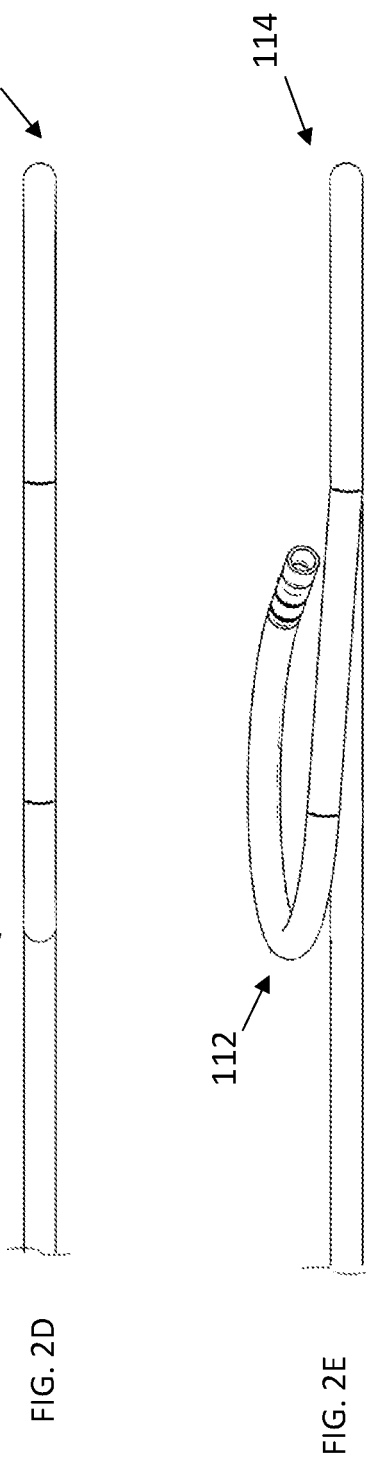
FIG. 2E is similar to FIG. 2D, but shows an alternative embodiment in which the longitudinal axes of the shaft in the proximal and distal curves lie in different planes.
Figure 3A:
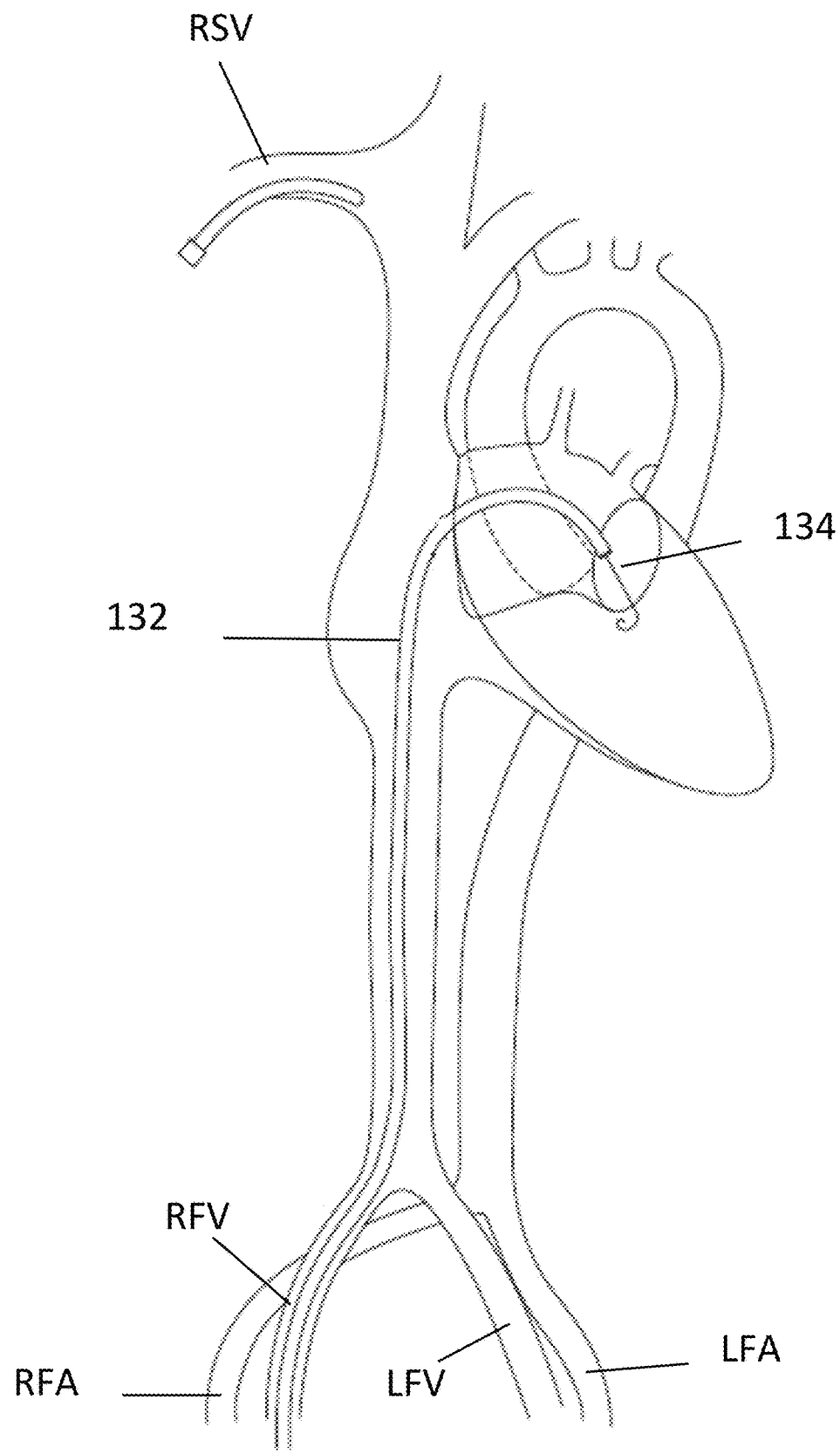
Figure 3B:
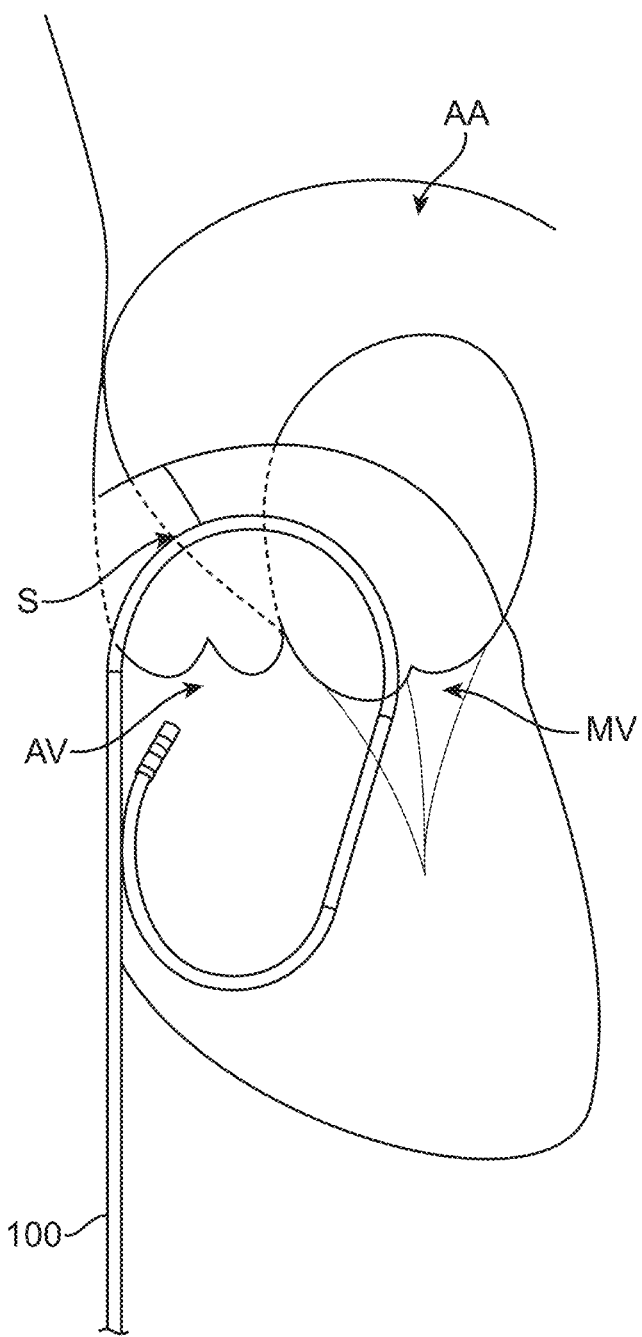
FIG. 3B illustrates positioning of the RLC after its distal tip has passed through the mitral valve into the left ventricle.

In the embodiment that is shown in FIG. 2A, the widest lateral dimension of the proximal curve 114, taken in a direction perpendicular to the longitudinal axis of the main shaft of the conduit, is wider than the widest lateral dimension of the distal curve 112 taken in a direction perpendicular to the longitudinal axis of the main shaft of the conduit. However, in other embodiments these widths may be approximately equal (for example, as shown in FIG. 2C) but the curvature would be ideally selected to orient the distal tip 118 towards the interior of the loop, thus ensuring that when the RLC is positioned with its distal tip in the left ventricle, the tip is generally oriented towards the aorta as shown in FIG. 3B.

The circumference of the curve 112 passes closely adjacent to the straight section of the main body of the main shaft in distal region 104, so that the main body extends tangentially with respect to the circumference of the proximal curve 114. The curvature of the proximal curve continues beyond this tangential area, so that the distal tip 118 is disposed within a generally enclosed loop as noted above. In other embodiments, the proximal curve and/or the distal tip may cross the straight section of the shaft.

The materials for the RLC are selected to give the conduit sufficient column strength to be pushed through the vasculature, torqued to orient its tip towards the aortic valve, and tracked over a wire, and it should have properties that prevent the distal loop 110 from permanently deforming as it is tracked over a wire. Although the distal loop 110 is moved out of its pre-shaped loop configuration to track over the wire, it is important that the shape-setting of the curves be retained. Otherwise the performance benefits of the distal loop's shape which, as evident from the Method description below are to aid proper movement into and through the mitral valve, to orient the tip of the RLC towards the aortic valve, and to track over the wire all the way to the descending aorta will not be realized.

Preferred material properties for the RLC will next be given, although materials having different properties may be used without departing from the scope of the invention. The shaft includes an outer jacket formed suitable polymeric material (e.g. polyether block amide, "PEBA," such as that sold under the brand name Pebax). A wire braid extends through shaft portions 108, 106 and most of 104 to enhance the torqueability of the RLC. A lubricious liner made using PTFE, ultra-high molecular weight polyethylene (UHMWPE), or like material also extends through these sections, allowing smooth relative movement between the RLC and the wire and cable that pass through it. The braid and liner terminate in the distal tip 118 as will be described with respect to FIG. 2B. The liner, braid and outer jacket are preferably subjected to a reflow process to create a composite material.

The most proximal portion 108 of the RLC, which may be between 450 and 550 mm in length (most preferably between 485 and 525 mm), is preferably formed from a relatively stiff material made from, as one example, 72D Pebax. Adjacent to the proximal portion 108 is the intermediate portion 106. This portion may have a length greater than 485 mm, or more preferably between 500-600 mm (most preferably between 530-570 mm), and it is preferably formed of fairly stiff material, but one that is more flexible than that used for the most proximal portion. As one example, this material may be 55D Pebax. These materials give the proximal and intermediate portions 108, 106 sufficient column strength and torqueability needed for its intended use.

Shaft section 104 is designed to be more flexible that the more proximal sections, because it must be able to pass through the heart during use. This section may be formed of a material such as 40D Pebax, although it is more preferably formed of a blend of 40D and 55D Pebax. This avoids an abrupt transition at the junction between sections 104 and 106 and can help to avoid kinking at that junction. The ratio of 40D to 55D material in the blend may be 50:50 or an alternative ratio. Shaft section 104 makes up the most distal part of the straight section of the main shaft, as well as both the distal and proximal curves 112, 114. The length of shaft section 104 is preferably between 510 and 610 mm, and more preferably between 540 and 580 mm.

A preferred configuration for the distal tip 118 will next be described. Referring to FIG. 2B, which is partially cut away to show features below the outer extrusion, the distal tip 118 includes an atraumatic distalmost section 120 formed of soft 35D Pebax or similarly soft material. Just proximal to the distal most section is a more rigid section (e.g. 55D Pebax) 122, which includes a radiopaque marker band 124 (e.g. PtIr) and the distal-most part of the lubricious liner 126. In the next most proximal section 130 is the terminal portion of the braid 128, which is covered by a more rigid material such as 72D polyethylene or similar material. Each of the sections 120, 122, 130 is very short in length, and preferably between 2-4 mm. As shown, the distal tip is preferably a generally straight section of the RLC extending from the distal curve 112.

It should be pointed out that while a number of preferred features for the RLC have been described above, alternative embodiments of the RLC might use any sub-combination of the above-described features alone or with other features not described here.

Method of Use

A method of placing the RLC via transseptal catheterization will next be described. The purpose of RLC placement is to position a conduit extending into a femoral vein and across the heart via the interatrial septum, through the mitral valve into the left ventricle, and then oriented towards the aortic valve. The RLC is then advanced through the aortic valve, beyond the coronary sinuses and through the ascending and descending aorta. In that position it enables a user to deploy an arterio-venous cable in the descending aorta that can be used to deliver other devices into the heart in procedures such as those discussed in the Background section of this application.

As an initial step, the practitioner obtains percutaneous access to the vessels that are to be used for the intravascular procedure. For the purposes of this discussion, it will be assumed that access to the right and or left femoral artery (RFA, LFA), the right or left femoral vein (RFV, LFV), and, if the procedure is one involving advancement of devices from a superior location (as discussed in the Background), the right subclavian vein (RSV) or the left subclavian vein (LSV), or the right or left internal jugular vein (RIJV, LIJV). One such sheath is shown in FIG. 3A, positioned in the RSV.

A Brockenbrough transseptal catheter 132 (BTC) is introduced through the RFV and, using the well-known technique of transseptal catheterization, is passed from the right atrium (RA) into the left atrium (LA). A wire 134, which may be an 0.035" wire such as the Abbott Versacore wire, is passed through the BTC and into the left atrium (LA). See FIG. 3A.

The BTC 132 is withdrawn at the RFV and exchanged for the RLC 100, which is advanced over the wire. The RLC preferably has been filled with an 80/20 saline-contrast solution for additional visibility under fluoroscopy. After it has crossed the inter-atrial septum into the LA, the RLC is advanced toward the lateral edge of the LA. From this position the wire is withdrawn proximally into the RLC (away from the loop 110, labeled in FIGS. 1 and 2A). The RLC is rotated counterclockwise about the axis of the main body portion as the wire is slowly withdrawn. This causes the tip to drop in an inferior direction into and through the mitral valve MV towards the left ventricle LV. Once the tip is through the MV, the RLC continues to be advanced, its shape causing the distal end of the tip to move in a right-ward (the patient's right) and anterior direction. This direction of motion is needed to orient the tip 118 towards the aortic valve AV, since the aortic valve is anterior and to the right of the mitral valve. FIG. 3B shows the distal tip of the RLC pointed towards the aortic valve. As shown, section 104 of the RLC extends within the inferior vena cava (not shown), extends through the inter-atrial septum S, drops into the mitral valve and forward into the left ventricle. Note with regard to this drawing that the distal curve 112 is positioned anterior (out of the plane of the drawing towards the viewer) with respect to the proximal curve.

Figure 4:
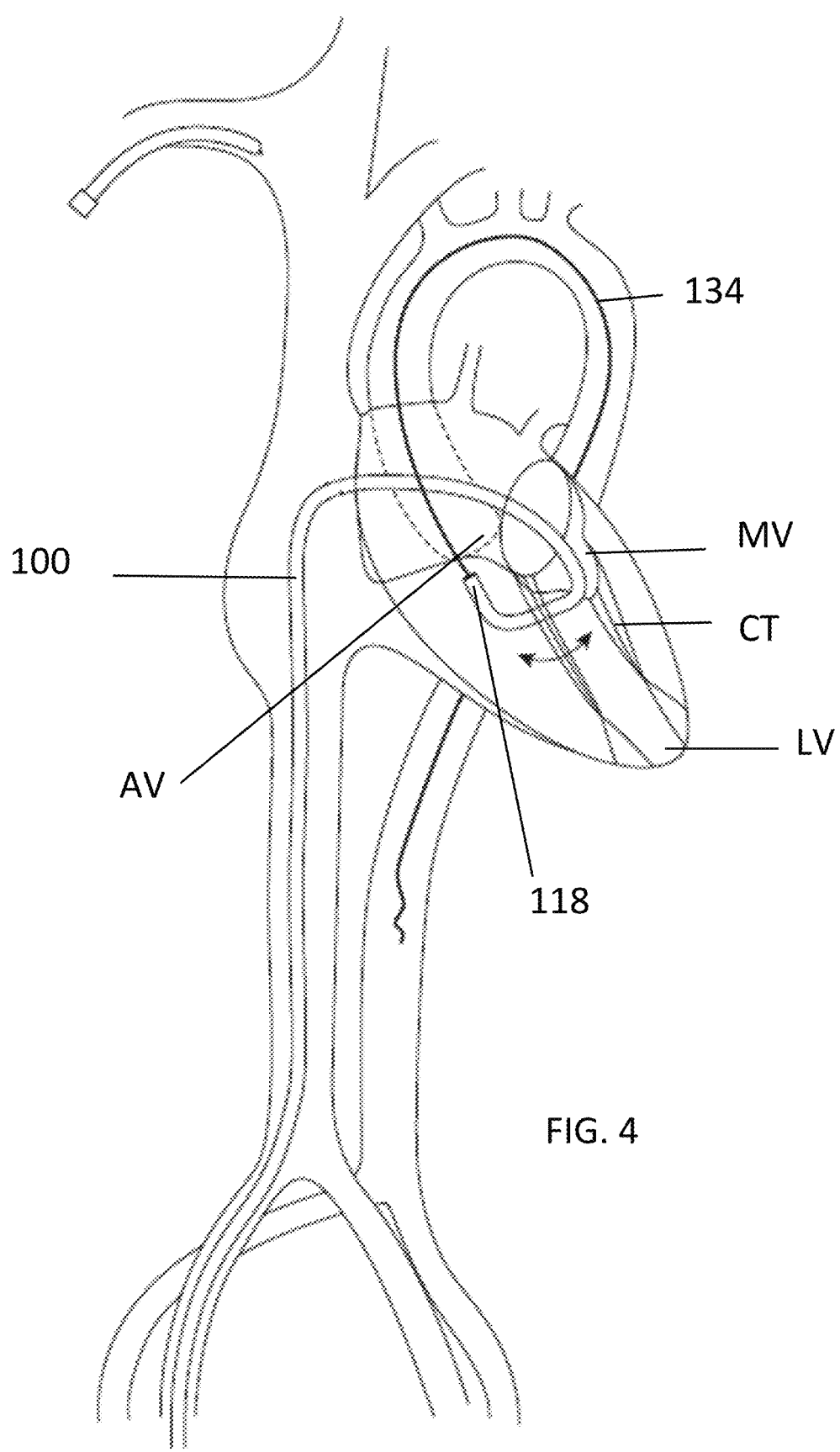

The practitioner may, at this point, wish to verify that the RLC tip is not trapped by the chordae tendineae CT of the mitral valve. This may be done by observing the fluoroscopic image and confirming the presence of a "windshield wiper" movement of the RLC tip, as such movement suggests that the tip is not entangled in the chordae. The arrows in FIG. 4 represent the "windshield wiper" motion of the distal tip of the RLC. Although the wire is shown in this drawing, the step of observing this motion of the distal tip is ideally performed before the wire is re-extended from the RLC.

When the distal tip 118 of the RLC 100 positioned in the LV, its curvature directs its tip towards the aortic valve as shown in FIG. 4. With the RCL positioned in this way, the guide wire 134 is advanced through the aortic valve, around the aortic arch, and into the descending aorta.

Figure 5:
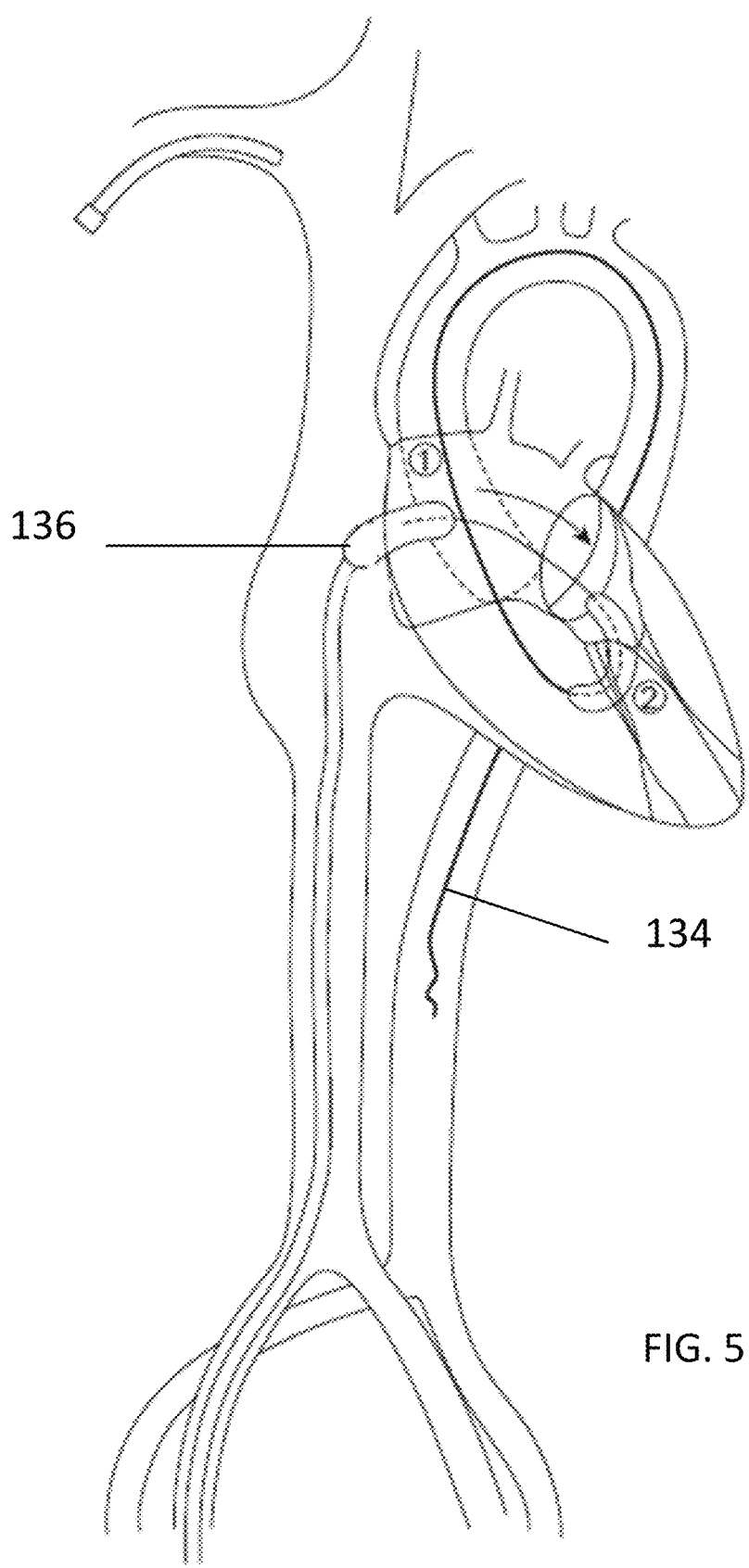

The RLC 100 is removed, leaving the wire 134 in place. A balloon dilation catheter 136 is advanced over the wire 134 to dilate the interatrial septum (atrial septostomy)—see balloon position (1) in FIG. 5. A balloon that may be used for this purpose is the 12×20 mm Boston Scientific Mustang balloon dilation catheter or the tracker balloon described in co-pending application Ser. No. 16,578,375. Following this, as a second step, the inflated balloon catheter is advanced further over the wire and through the mitral valve apparatus—see balloon position (2) in FIG. 5—to the aortic valve to further confirm that the wire path is free of the chordae entrapment.

Figure 6:
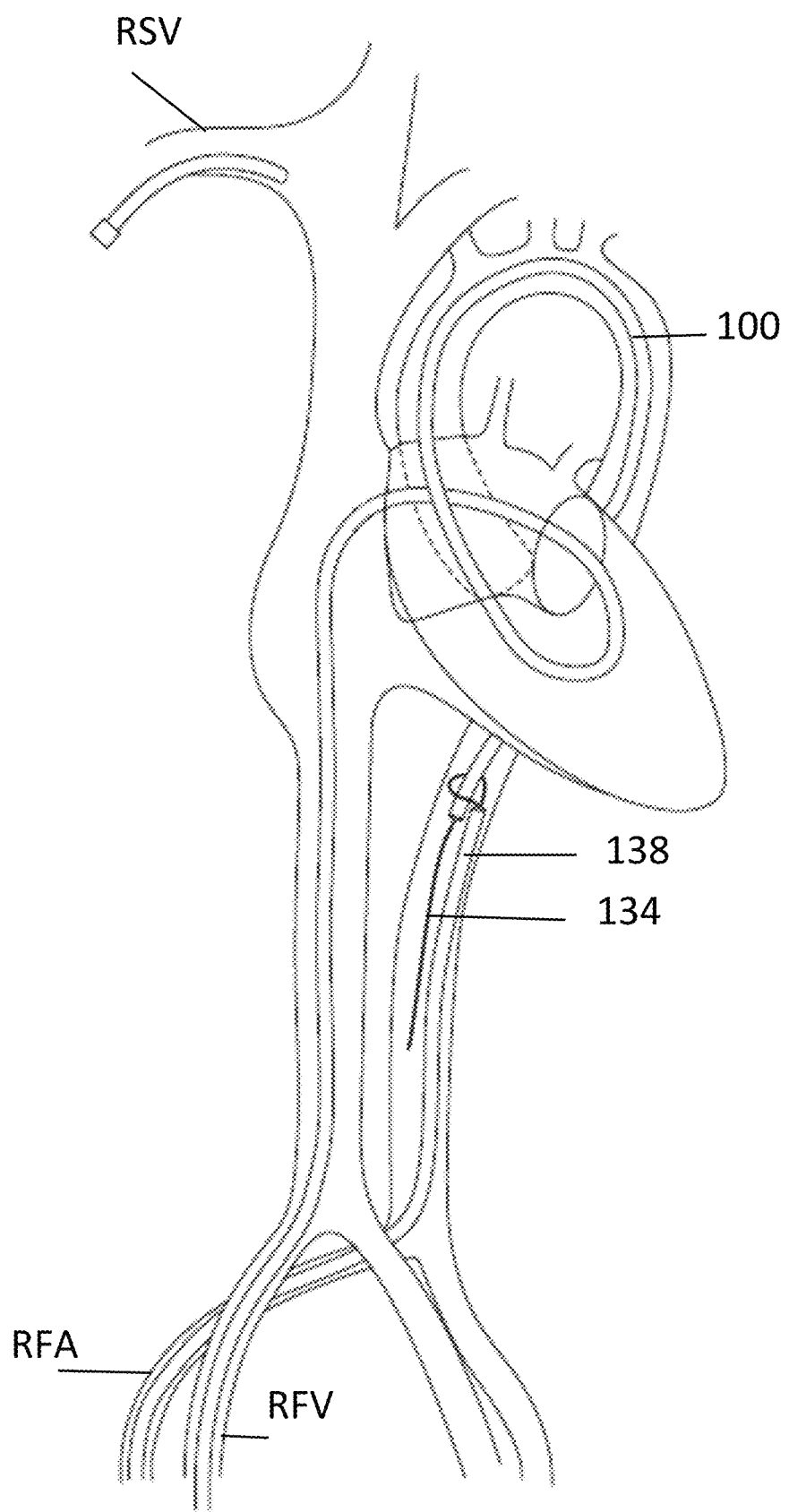

The balloon catheter is removed and replaced over the wire 134 with the RLC 100, which is reintroduced and then advanced all the way to the descending aorta as shown in FIG. 6.

A snare 138 is inserted in the RFA and used to capture the wire 134 in the descending aorta. The subsequent steps from this point may differ depending on the procedure that is to be performed. The steps that will next be described assume that the procedure involves placement of a cable to extend between the venous and arterial vasculature as described in the Background section, With the wire 134 loose in the snare, the snare is advanced upward in the aorta and allowed to slide over the RLC 100 as shown in FIG. 6.

With the snare secured on the RLC, the wire is withdrawn from the RFV and is exchanged for the cable (not shown) that is to be used. The cable is advanced the full length of the RLC, which remains in the position shown in FIG. 6. When the cable emerges from the RLC in the descending aorta, the snare 134 is pulled off the end of the RLC and used to capture the cable. The snare is exteriorized from the RFA to draw the end of the cable that is proximal to the RFA out the RFA. At this point both the cable and RLC extend from the RFV to the RFA. The steps that happen next are dependent on whether the end of the cable that is on the venous side needs to be access from a superior site or a femoral site. If a procedure to deliver a mitral valve therapeutic device, such as that described in PCT application WO/2018/098210, is to be carried out, the subsequent steps are performed using the cable extending between the RFV and RFA. If a procedure to deliver a pVAD is to be carried out, the cable may be exteriorized from the RSV using steps described in Commonly owned application Ser. No. 16,578,375, Systems and Methods for Transseptal Delivery of Percutaneous Ventricular Assist Devices and Other Non-Guidewire Based Transvascular Therapeutic Devices.

All patents and patent applications referred to herein, including for purposes of priority, are fully incorporated herein by reference.

We claim:

1. A conduit for creating a passage from a right atrium to a left atrium, through a mitral valve into the left ventricle, the conduit comprising:
   an elongate tubular member having a main body with a proximal portion and a distal portion distal to the proximal portion, the distal portion including a distal loop section having a proximal curve, a distal curve, a generally straight segment extending between the proximal and distal curves, and a distal tip, wherein the distal loop section curves back on itself,
   wherein the distal portion has a length of at least 500 mm and is formed of a polymeric material having a hardness of between 40D and 50D along its length, and wherein the proximal portion is formed of a polymeric material having greater stiffness than the distal portion.

2. The conduit of claim 1, wherein the proximal and distal curves have shapes selected to direct the distal tip into a mitral valve after it has crossed an inter-atrial septum from a right atrium to a left atrium of a heart, and to orient a distal opening of the distal tip towards an aortic valve of the heart when the straight segment or the distal curve is in the mitral valve and the distal tip is in a left ventricle.

3. The conduit of claim 1, wherein a widest lateral dimension of the distal curve taken in a direction perpendicular to a longitudinal axis of the main body is smaller than a widest lateral dimension of the proximal curve taken in a direction perpendicular to the longitudinal axis of the main body of the conduit.

4. The conduit of claim 1, wherein a widest lateral dimension of the distal curve taken in a direction perpendicular to a longitudinal axis of the main body is approximately equal to a widest lateral dimension of the proximal curve taken in a direction perpendicular to the longitudinal axis of the main body of the conduit.

5. The conduit of claim 1, wherein lengths of radii of the distal and proximal curves, a length of the generally straight segment along a longitudinal axis of said generally straight segment, a widest lateral dimension of the distal loop section taken in a direction perpendicular to a longitudinal axis of the main body of the conduit, and a longitudinal length L of the distal loop section taken in a direction parallel to a longitudinal axis of the main body are proportioned so that when the proximal curve is within mitral valve, the distal curve seats near a left ventricular apex and the distal tip is oriented towards, and in close proximity to, an aortic valve.

6. The conduit of claim 5, wherein the distal tip is enclosed within the distal loop section, bounded by the distal and proximal curves, the generally straight segment, and a part of the main body that is proximal to the proximal curve.

7. The conduit of claim 1, wherein the generally straight segment has a length selected to cause the distal curve to be positioned near a left ventricular apex and the distal tip to be positioned in close proximity to an aortic valve when the proximal curve is within a mitral valve.

8. The conduit of claim 1, wherein the distal loop section is a generally enclosed loop.

9. The conduit of claim 1, wherein the main body has a generally straight section proximal to the distal loop section and wherein an edge of the proximal curve passes closely adjacent to said generally straight section so that said generally straight section of the main body extends tangentially with respect to the proximal curve.

10. The conduit of claim 9, wherein the second generally straight section orients the distal tip away from the main body.

11. The conduit of claim 1, wherein the distal curve has smaller radius than the proximal curve, so that the distal loop section has a width that tapers from a distal to a proximal direction.

12. The conduit of claim 1, wherein the conduit includes a second generally straight section on which the distal tip is positioned.

13. The conduit of claim 1, wherein the elongate member has a longitudinal axis that includes a distal curve portion extending through the distal curve and a proximal curve portion extending through the proximal curve, and wherein the elongate member is shape set such that the distal curve portion of the longitudinal axis and the proximal curve portion of the longitudinal axis lie in a common plane.

14. The conduit of claim 1, wherein the elongate member has a longitudinal axis that includes a distal curve portion extending through the distal curve and a proximal curve portion extending through the proximal curve, and wherein the elongate member is shape set such that the distal curve portion of the longitudinal axis and the proximal curve portion of the longitudinal axis lie in different planes.

15. The conduit of claim 1, wherein the proximal portion of the elongate member is formed using a polymeric material of 72D durometer, the elongate member includes an intermediate portion distally adjacent to the proximal portion formed using a polymeric material of durometer of 55D, and wherein the distal portion is distal to the intermediate portion and is formed using a blend of 40D and 55D durometer polymeric material along its length.

16. The conduit of claim 15 wherein a ratio of 40D material and 55D material in the distal portion is 50:50.

17. The conduit of claim 15, wherein the distal tip is formed of lower durometer material than the distal loop section.

18. The conduit of claim 15, wherein the proximal portion has a length of at least 450 mm, and the intermediate portion has a length of at least 485 mm.

* * * * *